US012605314B2

(12) United States Patent
Singleton

(10) Patent No.: US 12,605,314 B2
(45) Date of Patent: Apr. 21, 2026

(54) BROAD-SPECTRUM, MINERAL, PHOTOPROTECTIVE COMPOSITIONS

(71) Applicant: LCS Advanced Solutions, LLC, Inglewood, CA (US)

(72) Inventor: Laura C. Singleton, Inglewood, CA (US)

(73) Assignee: LCS Advanced Solutions, LLC, Inglewood, CA (US)

(*) Notice: Subject to any disclaimer, the term of this patent is extended or adjusted under 35 U.S.C. 154(b) by 143 days.

(21) Appl. No.: 18/357,695

(22) Filed: Jul. 24, 2023

(65) Prior Publication Data

US 2023/0381072 A1 Nov. 30, 2023

Related U.S. Application Data

(63) Continuation of application No. 15/934,312, filed on Mar. 23, 2018, now abandoned.

(51) Int. Cl.

| | |
|---|---|
| ***A61Q 17/04*** | (2006.01) |
| ***A61K 8/06*** | (2006.01) |
| ***A61K 8/25*** | (2006.01) |
| ***A61K 8/27*** | (2006.01) |
| ***A61K 8/29*** | (2006.01) |
| ***A61K 8/891*** | (2006.01) |
| ***A61K 8/96*** | (2006.01) |

(52) U.S. Cl.

CPC ................ *A61K 8/27* (2013.01); *A61K 8/064* (2013.01); *A61K 8/25* (2013.01); *A61K 8/29* (2013.01); *A61K 8/891* (2013.01); *A61K 8/96* (2013.01); *A61Q 17/04* (2013.01); *A61K 2800/412* (2013.01)

(58) Field of Classification Search

CPC .......... A61Q 17/04; A61Q 19/00; A61K 8/06; A61K 8/064; A61K 8/29; A61K 8/27; A61K 9/0014; A61K 2800/10; A61K 8/25

See application file for complete search history.

(56) References Cited

U.S. PATENT DOCUMENTS

| | | | |
|---|---|---|---|
| 2,435,005 | A | 1/1948 | Huppke |
| 3,175,950 | A | 3/1965 | Abraham |
| 3,479,428 | A | 11/1969 | Bryce |
| 4,144,325 | A | 3/1979 | Voyt |
| 4,663,157 | A | 5/1987 | Brock |
| 4,671,955 | A | 6/1987 | Palinczar |
| 4,707,354 | A | 11/1987 | Garlen |
| 4,710,371 | A | 12/1987 | Palinczar |
| 4,847,071 | A | 7/1989 | Bissett |
| 5,000,937 | A | 3/1991 | Grollier |
| 5,093,107 | A | 3/1992 | Matravers |
| 5,116,604 | A | 5/1992 | Fogel |
| 5,223,250 | A | 6/1993 | Mitchell |
| 5,229,104 | A | 7/1993 | Sottery |
| 5,256,403 | A | 10/1993 | Gaskin |
| 5,340,567 | A | 8/1994 | Cole |
| 5,468,471 | A | 11/1995 | Zecchino |
| 5,516,457 | A | 5/1996 | Dahms |
| 5,543,136 | A | 8/1996 | Aldous |
| 5,560,917 | A | 10/1996 | Cohen |
| 5,599,533 | A | 2/1997 | Stepniewski |
| 5,618,521 | A | 4/1997 | de Rigal |
| 5,665,368 | A | 9/1997 | Lentini |
| 5,670,139 | A | 9/1997 | Allard |
| 5,744,126 | A | 4/1998 | Horino |
| 5,783,173 | A | 7/1998 | Bonda |
| 5,788,954 | A | 8/1998 | Bonda |
| 5,817,298 | A | 10/1998 | Galley |
| 5,849,273 | A | 12/1998 | Bonda |
| 5,876,699 | A | 3/1999 | DiSomma |
| 5,883,085 | A | 3/1999 | Blank |
| 5,928,660 | A | 7/1999 | Kobayashi |
| 5,935,336 | A | 8/1999 | Sandhu |
| 5,935,556 | A | 8/1999 | Tanner |
| 5,939,054 | A | 8/1999 | Msika |
| 5,945,090 | A | 8/1999 | Randall |
| 6,139,823 | A | 10/2000 | Drechsler |
| 6,200,964 | B1 | 3/2001 | Singleton |

(Continued)

FOREIGN PATENT DOCUMENTS

| | | |
|---|---|---|
| AT | 224177 | 11/1962 |
| AU | 576863 | 9/1988 |

(Continued)

OTHER PUBLICATIONS

Chen D., et al. "Synthesis of monodisperse mesoporous titania beads with controllable diameter, high surface areas and variable pore diameters (14-23 nm)." J Am Chem Soc. Mar. 4, 2010;132(12):4438-44. doi: 10.1021/ja100040p. PMID: 20201515.

(Continued)

*Primary Examiner* — Tracy Liu

(74) *Attorney, Agent, or Firm* — Transformative Legal; Len S. Smith; Julie E. Kurzrok

(57) ABSTRACT

Broad-spectrum mineral sunscreen compositions comprising (a) a formulation component comprising (I) a water-in-oil emulsifier component comprising at least one polyglyceryl fatty acid ester compound containing 3-6 glycerin units, (II) two film-forming polymers, e.g., copolymers of dimethicone, (b) a siliceous compound component consisting of two siliceous compounds (I) an amorphous spherical silica component, and (II) a mixture of diatomaceous algae materials comprising materials from at least two of *Fragilaria zeilleri, Gomphonema angustatum, Navicula radiosa*, and *Cyclotella andancensis* (c) a sunscreen active ingredient component comprising (I) two photoprotective metal oxides that block, reflect, refract or otherwise attenuate ultraviolet radiation comprising (A) highly porous zinc oxide particles having an average particle size of greater than about 100 nanometers and infiltrated by the formulation component (B) and titanium dioxide particles, wherein the composition is non-whitening when applied to the skin of a person with Fitzpatrick Skin Types I-IV.

17 Claims, No Drawings

(56) References Cited

U.S. PATENT DOCUMENTS

| | | | |
|---|---|---|---|
| 6,248,340 | B1 | 6/2001 | Maor |
| 6,252,100 | B1 | 6/2001 | Herzig |
| 6,309,627 | B1 | 10/2001 | Golz-Berner |
| 6,322,776 | B1 | 11/2001 | Ortega, II |
| 6,326,013 | B1 | 12/2001 | Lemann |
| 6,350,894 | B1 | 2/2002 | Bonda |
| 6,361,816 | B1 | 3/2002 | Amari |
| 6,384,023 | B2 | 5/2002 | Singleton |
| 6,699,464 | B1 | 3/2004 | Popp |
| 6,830,746 | B2 | 12/2004 | SaNogueira |
| 6,906,106 | B2 | 6/2005 | Chevalier |
| 6,942,878 | B2 | 9/2005 | Ishii |
| 7,014,842 | B2 | 3/2006 | Dueva-Koganov |
| 7,029,660 | B2 | 4/2006 | Anja |
| 7,034,073 | B2 | 4/2006 | Asaine |
| 7,175,834 | B2 | 2/2007 | Aust |
| 7,182,938 | B2 | 2/2007 | Andre |
| 7,276,230 | B2 | 10/2007 | Gonzalez |
| 7,407,666 | B2 | 8/2008 | Tarletsky |
| 7,427,690 | B2 | 9/2008 | Gupta |
| 7,481,845 | B2 | 1/2009 | De La Mettrie |
| 7,892,570 | B2 | 2/2011 | Elliott |
| 8,236,287 | B2 | 8/2012 | Singleton |
| 8,241,613 | B2 | 8/2012 | Candau |
| 8,637,057 | B2 | 1/2014 | Patel |
| 8,642,018 | B2 | 2/2014 | Kurosawa |
| 8,647,609 | B2 | 2/2014 | Kim |
| 8,697,035 | B2 | 4/2014 | Singleton |
| 8,795,696 | B2 | 8/2014 | Milora |
| 9,034,302 | B2 | 5/2015 | Gray |
| 9,060,942 | B2 | 6/2015 | Harada |
| 9,139,737 | B1 | 9/2015 | Shah |
| 9,192,547 | B2 | 11/2015 | Fukuhara |
| 9,333,159 | B2 | 5/2016 | Hayes |
| 9,487,409 | B2 | 11/2016 | Sueda |
| 9,517,190 | B2 | 12/2016 | Johncock |
| 9,642,785 | B2 | 5/2017 | Itagaki |
| 9,649,263 | B2 | 5/2017 | Youssef |
| 9,744,111 | B2 | 8/2017 | Norman |
| 10,029,127 | B2 | 7/2018 | Gaudry |
| 10,045,918 | B2 | 8/2018 | Gershon |
| 10,092,494 | B2 | 10/2018 | Sanogueira |
| 10,124,030 | B2 | 11/2018 | Goldsberry |
| 10,183,868 | B2 | 1/2019 | McCormick |
| 10,238,585 | B2 | 3/2019 | Ishida |
| 10,357,569 | B2 | 7/2019 | Busch |
| 10,383,811 | B1 | 8/2019 | Patel |
| 10,434,048 | B2 | 10/2019 | Dudley |
| 10,813,870 | B2 | 10/2020 | Shah |
| 10,959,924 | B2 | 3/2021 | Gershon |
| 11,213,463 | B2 | 1/2022 | Kubota |
| 11,426,336 | B2 | 8/2022 | Zickerman |
| 11,458,090 | B2 | 10/2022 | Josephson |
| 11,707,422 | B2 | 7/2023 | Rigg |
| 2001/0018432 | A1 | 8/2001 | Singleton |
| 2002/0034524 | A1 | 3/2002 | Poret |
| 2002/0114773 | A1 | 8/2002 | Kanji |
| 2002/0155073 | A1 | 10/2002 | Fankhauser |
| 2002/0155962 | A1 | 10/2002 | Cincotta |
| 2003/0059383 | A1 | 3/2003 | SaNogueira |
| 2003/0072723 | A1 | 4/2003 | Gers-Barlag |
| 2003/0161795 | A1 | 8/2003 | Tsuzuki |
| 2003/0170280 | A1 | 9/2003 | Canham |
| 2003/0219391 | A1 | 11/2003 | Liew |
| 2004/0028709 | A1 | 2/2004 | Dueva |
| 2004/0091433 | A1 | 5/2004 | Buchholz |
| 2004/0126337 | A1 | 7/2004 | Singleton |
| 2004/0146539 | A1 | 7/2004 | Gupta |
| 2004/0219124 | A1 | 11/2004 | Gupta |
| 2005/0136012 | A1 | 6/2005 | Gonzalez |
| 2005/0175562 | A1 | 8/2005 | Hadasch |
| 2005/0209131 | A1 | 9/2005 | Singleton |
| 2006/0045890 | A1 | 3/2006 | Gonzalez |
| 2006/0067904 | A1 | 3/2006 | Russ |
| 2006/0110415 | A1 | 5/2006 | Gupta |
| 2006/0115439 | A1 | 6/2006 | Lu |
| 2006/0216258 | A1 | 9/2006 | Singleton |
| 2007/0009453 | A1 | 1/2007 | Willemin |
| 2007/0010408 | A1 | 1/2007 | Hobuaki |
| 2007/0085063 | A1 | 4/2007 | Capelli |
| 2007/0149395 | A1 | 6/2007 | Kroell |
| 2007/0160549 | A1 | 7/2007 | Hunt |
| 2007/0196309 | A1 | 8/2007 | Tarletsky |
| 2007/0218021 | A1 | 9/2007 | Wells |
| 2007/0243143 | A1 | 10/2007 | Patil |
| 2007/0280895 | A1 | 12/2007 | Weimer |
| 2008/0081024 | A1 | 4/2008 | Beasley |
| 2008/0213200 | A1 | 9/2008 | Vromen |
| 2008/0226727 | A1 | 9/2008 | Kessell |
| 2009/0010971 | A1 | 1/2009 | Shio |
| 2009/0041691 | A1 | 2/2009 | Candau |
| 2009/0041712 | A1 | 2/2009 | Singleton |
| 2009/0162443 | A1 | 6/2009 | Anthony |
| 2009/0202459 | A1 | 8/2009 | Spaulding |
| 2009/0258068 | A1 | 10/2009 | Shio |
| 2009/0297461 | A1 | 12/2009 | Perle |
| 2010/0061947 | A1 | 3/2010 | Schlossman |
| 2010/0129299 | A1 | 5/2010 | Singleton |
| 2010/0202985 | A1 | 8/2010 | SenGupta |
| 2010/0310871 | A1 | 12/2010 | McCormick |
| 2010/0316582 | A1 | 12/2010 | Tsuzuki |
| 2011/0110990 | A1 | 5/2011 | Yu |
| 2011/0293543 | A1 | 12/2011 | Yu |
| 2012/0014882 | A1 | 1/2012 | Singleton |
| 2012/0015013 | A1 | 1/2012 | Schlossman |
| 2012/0058192 | A1 | 3/2012 | Singleton |
| 2012/0219515 | A1 | 8/2012 | Barrett |
| 2012/0258055 | A1 | 10/2012 | Gray |
| 2012/0263661 | A1 | 10/2012 | Grune |
| 2012/0288449 | A1 | 11/2012 | Singleton |
| 2013/0011348 | A1 | 1/2013 | Takakura |
| 2013/0022655 | A1 | 1/2013 | Sachweh |
| 2013/0028851 | A1 | 1/2013 | Fontaine |
| 2013/0052148 | A1 | 2/2013 | Chavan |
| 2013/0089507 | A1 | 4/2013 | Milora |
| 2013/0089588 | A1 | 4/2013 | Milora |
| 2013/0095050 | A1 | 4/2013 | Daly |
| 2014/0004165 | A1 | 1/2014 | Novejarque Conde |
| 2014/0335137 | A1 | 11/2014 | Hayes |
| 2015/0064224 | A1 | 3/2015 | Tong |
| 2015/0086633 | A1 | 3/2015 | Sakanishi |
| 2015/0202145 | A1 | 7/2015 | Friedman |
| 2015/0265510 | A1 | 9/2015 | Johncock |
| 2015/0283059 | A1 | 10/2015 | Nagare |
| 2015/0376025 | A1 | 12/2015 | McCormick |
| 2016/0058681 | A1 | 3/2016 | Li |
| 2016/0206527 | A1 | 7/2016 | Hueber |
| 2016/0220457 | A1 | 8/2016 | Yamaguchi |
| 2016/0303020 | A1 | 10/2016 | Blachechen |
| 2016/0367448 | A1 | 12/2016 | Youssef |
| 2017/0030938 | A1 | 2/2017 | She |
| 2017/0181941 | A1 | 6/2017 | Gunawan |
| 2017/0189296 | A1 | 7/2017 | SaNogueira |
| 2018/0116925 | A1 | 5/2018 | Johnson |
| 2018/0185254 | A1 | 7/2018 | Jung |
| 2018/0235855 | A1 | 8/2018 | Schlossman |
| 2018/0311117 | A1 | 11/2018 | Zeng |
| 2018/0353402 | A1 | 12/2018 | Fisher |
| 2019/0016754 | A1 | 1/2019 | Patwari |
| 2019/0183754 | A1 | 6/2019 | Singleton |
| 2019/0290560 | A1 | 9/2019 | Singleton |
| 2020/0157364 | A1 | 5/2020 | Shah |
| 2020/0247684 | A1 | 8/2020 | Suvaci |
| 2020/0306162 | A1 | 10/2020 | Ahmad |
| 2020/0390665 | A1 | 12/2020 | El Achkar |
| 2021/0000704 | A1 | 1/2021 | Shao |
| 2021/0038494 | A1 | 2/2021 | Qu |
| 2021/0052474 | A1 | 2/2021 | Fujinohara |
| 2021/0059911 | A1 | 3/2021 | Paulucci |
| 2021/0154106 | A1 | 5/2021 | Mecca |
| 2021/0244631 | A1 | 8/2021 | Fernandes |
| 2021/0315781 | A1 | 10/2021 | Mito |
| 2021/0353514 | A1 | 11/2021 | Patel |
| 2022/0000732 | A1 | 1/2022 | Li |

(56) References Cited

U.S. PATENT DOCUMENTS

| | | | |
|---|---|---|---|
| 2022/0008300 | A1 | 1/2022 | Lee |
| 2022/0023161 | A1 | 1/2022 | Milora |
| 2023/0080141 | A1 | 3/2023 | Stahl |
| 2023/0121763 | A1 | 4/2023 | Zachary |
| 2023/0147073 | A1 | 5/2023 | Singleton |
| 2023/0165763 | A1 | 6/2023 | Shi |

FOREIGN PATENT DOCUMENTS

| | | | | |
|---|---|---|---|---|
| AU | 2003233396 | | 9/2003 | |
| AU | 2007221239 | | 9/2007 | |
| BR | PI0707029 | | 4/2011 | |
| CA | 1128864 | | 8/1982 | |
| CA | 2029240 | | 5/1992 | |
| CA | 2168869 | | 3/1995 | |
| CA | 2642783 | | 9/2007 | |
| CA | 2643321 | | 9/2007 | |
| CA | 2710958 | | 7/2009 | |
| CA | 2913545 | | 5/2016 | |
| CN | 104224650 | | 12/2014 | |
| CN | 110302071 | | 10/2019 | |
| DE | 60000474 | | 3/2003 | |
| DE | 69820243 | | 9/2004 | |
| EP | 0383540 | | 8/1990 | |
| EP | 0427411 | | 5/1991 | |
| EP | 0463030 | | 1/1992 | |
| EP | 0583308 | | 2/1994 | |
| EP | 0590014 | | 4/1994 | |
| EP | 0678015 | | 10/1995 | |
| EP | 0765656 | | 4/1997 | |
| EP | 0628303 | B1 | 9/1997 | |
| EP | 1097695 | | 5/2001 | |
| EP | 1172083 | | 1/2002 | |
| EP | 1181329 | A1 | 2/2002 | |
| EP | 1421931 | | 5/2004 | |
| EP | 1435230 | A3 | 11/2004 | |
| EP | 1709953 | A1 | 10/2006 | |
| EP | 1796619 | | 6/2007 | |
| EP | 1855642 | A2 | 11/2007 | |
| EP | 1949886 | | 7/2008 | |
| EP | 1998737 | | 12/2008 | |
| EP | 2207525 | | 7/2010 | |
| EP | 2407148 | | 1/2012 | |
| EP | 2425810 | A2 | 3/2012 | |
| EP | 2509568 | B1 | 9/2014 | |
| EP | 2774481 | | 9/2014 | |
| EP | 2774604 | | 9/2014 | |
| EP | 2853255 | | 4/2015 | |
| EP | 3062769 | | 9/2016 | |
| EP | 3238704 | A1 | 11/2017 | |
| EP | 3624756 | | 11/2022 | |
| ES | 2183771 | | 4/2003 | |
| FI | 97685 | | 10/1996 | |
| FR | 2757380 | | 6/1998 | |
| FR | 2758985 | | 8/1998 | |
| FR | 2768926 | | 4/1999 | |
| FR | 2800605 | | 5/2001 | |
| FR | 3072291 | | 4/2019 | |
| FR | 3072292 | | 4/2019 | |
| GB | 1185943 | | 3/1970 | |
| GB | 1375436 | | 11/1974 | |
| GB | 1473483 | | 5/1977 | |
| GB | 1488061 | | 10/1977 | |
| GB | 2217987 | | 11/1989 | |
| GB | 2437056 | | 10/2007 | |
| JP | H07206645 | | 8/1995 | |
| JP | 2001172503 | | 6/2001 | |
| JP | 2006265253 | A | 10/2006 | |
| JP | 2009527571 | | 7/2009 | |
| KR | 20130134976 | | 12/2013 | |
| KR | 102203667 | B1 | 1/2021 | |
| NZ | 236318 | | 11/1993 | |
| NZ | 264108 | | 5/1997 | |
| WO | WO1993011742 | | 6/1993 | |
| WO | WO1994018940 | A | 9/1994 | |
| WO | WO1997003642 | | 2/1997 | |
| WO | WO1998052529 | | 11/1998 | |
| WO | WO2000064472 | | 11/2000 | |
| WO | WO2000073374 | A1 | 12/2000 | |
| WO | WO2002011717 | | 2/2002 | |
| WO | WO2007078062 | | 7/2007 | |
| WO | WO2007097967 | | 8/2007 | |
| WO | WO2007100689 | | 9/2007 | |
| WO | WO2008070368 | | 6/2008 | |
| WO | WO2008155080 | | 12/2008 | |
| WO | WO2009126722 | | 10/2009 | |
| WO | WO2010059620 | | 5/2010 | |
| WO | WO 2011111828 | | 9/2011 | |
| WO | WO2011116216 | | 9/2011 | |
| WO | WO2011150034 | | 12/2011 | |
| WO | WO2012009405 | A2 | 1/2012 | |
| WO | WO2012009405 | A3 | 3/2012 | |
| WO | WO2012104160 | | 8/2012 | |
| WO | WO 2013102060 | | 7/2013 | |
| WO | WO-2014129484 | A1 * | 8/2014 | ............ A61K 8/046 |
| WO | WO2015/0030702 | | 3/2015 | |
| WO | WO2015144331 | | 10/2015 | |
| WO | WO2015152865 | | 10/2015 | |
| WO | WO2016036828 | | 3/2016 | |
| WO | WO2016082061 | | 6/2016 | |
| WO | WO2017210406 | | 12/2017 | |
| WO | WO-2020216676 | A1 * | 10/2020 | ............ A61K 8/066 |
| WO | WO2021174715 | A1 | 9/2021 | |

OTHER PUBLICATIONS

Cole C, et al. "Metal oxide sunscreens protect skin by absorption, not by reflection or scattering." Photodermatol Photoimmunol Photomed. Jan. 2016;32(1):5-10. doi: 10.1111/phpp.12214. Epub Nov. 10, 2015. PMID: 26431814.

Geoffrey K, et al. "Sunscreen products: Rationale for use, formulation development and regulatory considerations." Saudi Pharm J. Nov. 2019;27(7):1009-1018. doi: 10.1016/j.jsps.2019.08.003. Epub Aug. 16, 2019. PMID: 31997908; PMCID: PMC6978633.

Lu P, et al. "Analysis of titanium dioxide and zinc oxide nanoparticles in cosmetics." J Food Drug Anal. Sep. 2015;23(3):587-594. doi: 10.1016/j.jfda.2015.02.009. Epub Apr. 20, 2015. PMID: 28911719; PMCID: PMC9351801.

Poluboyarinov A, et al. "Titanium Oxide Microspheres with Tunable Size and Phase Composition." Materials (Basel). May 7, 2019;12(9):1472. doi: 10.3390/ma12091472. PMID: 31067714; PMCID: PMC6539129.

Vivero-Escoto J, et al. "Recent progress in mesoporous titania materials: adjusting morphology for innovative applications." Sci Technol Adv Mater. Feb. 2, 2012;13(1):013003. doi: 10.1088/1468-6996/13/1/013003. PMID: 27877467; PMCID: PMC5090292.

U.S. Appl. No. 16/220,353, filed Jun. 20, 2019, Singleton, Laura C.

Access Ingredients. UV Absorbers. Mar. 8, 2015. <http://accessingredients.com/products/uv-absorbers/>. (Year: 2015).

FDA Sunscreen Monograph. "Labeling and Effectivness Testing; Sunscreen Drug Products for Over-the-Counter Human Use." vol. 76 Federal Reigster pp. 35620 (Jun. 17, 2011).

Afonso, S. et al. "Photodegradation of avobenzone: stabilization effect of antioxidants." J Photochem Photobiol B. vol. 140, pp. 36-40 (2014).

Akgul, G. "Structural properties of zinc oxide and titanium dioxide nanoparticles prepared by chemical vapor synthesis." Journal of Alloys and Compounds 554 (2013) 177-181. Published Dec. 6, 2012.

Allantoin Cream. "Uses, Side Effects, and More." Generic Name: Allantoin. WebMD. Accessed Jul. 5, 2023.

Avenel-Audran M. Archives of Dermatology. "Octocrylene, an emerging photoallergan." 2010. vol. 146, No. 7, pp. at pp. 753-757.

Beasley, DG et al. "Characterization of the UVA protection provided by avobenzone, zinc oxide, and titanium dioxide in broad-spectrum sunscreen products." Am J Clin Dermatol vol. 11, No. 6, pp. 413-421 (2010). Published Aug. 21, 2012.

HallBrite BHB from The Hallstar Company (Chicago, IL). https://www.hallstarbeauty.com/product/hallbrite-bhb/. Accessed Jul. 4, 2023.

(56) References Cited

OTHER PUBLICATIONS

Bennis, Chelsey. "Improving sunscreen compliance and awareness of skin cancer and the effects of the sun in adolescents and young adults: A quality improvement project." (2021).
Bhati, R. "A Detailed Review on Oral Mucosal Drug Delivery System." Mar. 1, 2012. International Journal of Pharmacuetical Sciences Research. Web of Sciences.
Bhatia, S. "Mycosporine and mycosporine-like amino acids: A paramount tool against ultra violet irradiation." Pharacognosy Review. Jul.-Dec. 2011; 5(10): 138-146.
Croda. Solaveil MicNo Personal Care Brochure. Oct. 10, 2022.
MicNo Product Overview and Catalogue. Apr. 21, 2021. Document ID 0321PCEP02526v1EN.
Solespheres from AGC Chemicals America, Inc. "Environmentally Safe Solesphere Microsphere Silica Gels Improve Visual and Tactile Aesthetics in Skincare Formulations." (Exton, Pennsylvania). Aug. 25, 2021.
Dispersun DSP OL 300 from Innospec Performance Chemicals (Salisbury, NC). Accessed on Jul. 4, 2023.
Sunsolv BOV from Innospec Performance Chemicals (Salisbury, NC). Accessed on Jul. 5, 2023.
Non-Final Office Action on Sep. 22, 2023 for U.S. Appl. No. 16/566,781 (LCS19371USVAZ).
Chrapusta, E. "Mycosporine-Like Amino Acids: Potential Health and Beauty Ingredients." Marine Drugs. Published Oct. 21, 2017.
Jungbunzlauer. "Citrofol Citrate Esters in Sunscreen Formulation." Advertorial. Basel, Switzerland. Sep. 8, 2021. https://www.sofw.com/en/news/latest-news/personal-care/2419-citrofol-citrate-esters-in-sunscreen-formulation.
Section 352.76 of Title 21 of the U.S. Code of Federal Regulations. "Determination if a product is water resistant or very water resistant." Accessed Jul. 4, 2023.
ARGAN Co. "Disbributor of Specialty Cosmetic Raw Materials." ARGA-SUN ZnO. Feb. 14, 2016.
Technical Data Sheets (TDS), ARGA-SUN ZnO CLR. Reviewed Feb. 19, 2019.
SunSpheres by the Dow Chemical Company (Midland, MI). Accessed on Jul. 4, 2023.
Jeechem International Corporation. Technical Bulletin. "Jeechem TDTM-MC Maximum Color for Maximum Wow." Accessed Apr. 18, 2018.
Organic Creations. "Panthenol DL Description." Accessed to Jul. 5 2023. https://organic-creations.com/product/panthenol-dl/.
Cross, S.E., et al. "Human Skin Penetration of Sunscreen Nanoparticles: In-vitro Assessment of a Novel Micronized Zinc Oxide Formulation." Skin Pharmacol. Physiol., vol. 20, pp. 148-154 (2007). Published online Jan. 17, 2007.
Culliney, K. (Mar. 10, 2020). "SPF+, whitening and perfecting: L'Oreal publishes flurry of sunscreen patents." https://www.cosmeticsdesign-europe.com/Article/2020/03/10/L-Oreal-sun-protection-patents-cover-SPF-skin-whitening-and-appearance.
CosmoSurf LS-1 Siltech. CE Series. Technical Data Sheet. (2009).
Covabead Crystal Technical Data Sheet (Mar. 14, 2014; revised Mar. 8, 2017).
Elix-Ir Technical Datasheet. Supplied by Lucas Meyer Cosmetics (IFF). Special Chem. https://cosmetics.specialchem.com/product/i-lucas-meyer-cosmetics-iff-elix-ir.
SkinSave Technical Data Sheet. Supplied by BIONAP (Bioactive Natural Products). Special Chem. Jun. 8, 2023. https://cosmetics.specialchem.com/product/i-bionap-bioactive-natural-products-skin-save. Must be Purchased.
Technical Data Sheet for EverZinc for Zano 10, Zano 20, & Zano (Nov. 25, 2016).
De Groot, A.C., and Roberts, D.W. "Contact and photocontact allergy to octocrylene: a review." Contact Dermatitis, vol. 70, pp. 193-204 (2014). First published Mar. 14, 2014.
Dumbuya et al. "Impact of Iron-Oxide Containing Formulations Against Visible Light-Induced Skin Pigmentation in Skin of Color Individuals." J Drug Dermatol. Jul. 2020; 19(7): 712-717. doi: 10.36849/JDD.2020.5032. Epub Jun. 18, 2020.
Elementis Bentone Gel PTM V (East Windor, NJ). Accessed on Jul. 4, 2023.
Fares, H.M. "Formulating Anhydrous Sunscreen products that Applies Clear on Skin that is Wet." Ashland Specialty Ingredients, 1005 Route 202/206, Bridgewater, NJ 08807. Accessed Apr. 16, 2018.
Fuller, A. "Sun care: beyond protection." Cosmetics; Mississauga vol. 28, Iss. 1, (Jan. 2000): 62.
Giannnakopoulou, T. "Optical and photocatalytic properties of composite TiO2/ZnO thin films." Catalysis Today. Oct. 28, 2013.
Plankton. "Plankton Glass Flower: The glass diamond from ancient volcanic lakes." Powerpoint. Nov. 30, 2017.
Australian Gold. "Botanicals Sunscreen 70 Minerals." (NDC 58443-0265; marketed starting Oct. 29, 2018). Https://www.australiangold.com/shop/product-line/botanical/botanical-spf-70-sunscreen-lotion.
Gulson, B. "A review of critical factors for assessing the dermal absorption . . . " Arch Toxicol (2015) 89: 1909-1930. doi: 10.1007/s00204-015-1564-z. Published Jul. 4, 2015.
SunSpheres. "Rohm and Haas Personal Care: ingredients of creativity." Hollow Sphere Technology. Powerpoint. Feb. 1, 2006.
Symire. "Multiple Benefits for Cosmetics with SymSave H." Jul. 26, 2013. Focus on Surfactants, vol. 13, Is. 10, p. 2. https://doi.org/10.1016/S1351-4210(13)70242-7.
Symrise. "Dragosine 844033: Multi-Functional Anti-Aging Peptide." Brochure (2014).
Symrise, Inc. "Symsave H." Accessed on Jul. 4, 2023.
Synrise, Inc. "SymRelief 100." Bisabolol (and) Zingiber Officinale (Ginger) Root Extract. Prospector. Https://www.ulprospector.com/en/na/PersonalCare/Detail/3030/216994/SymRelief-100. Accessed Jul. 4, 2023.
Symrise, Inc. "Corapan TQ." Teterboro, NJ. Accessed on Jul. 4, 2023.
Alzo International, Inc. "Elefac I-205." (Sayreville, NJ). Accessed Jul. 4, 2023.
Symrise, Inc. "Symdoil 68." Teterboro, NJ. Accessed on Jul. 4, 2023.
Access Ingredients. "AccessSIL FF-16." South Pasadena, CA. Accessed on Jul. 4, 2023.
Ishii, N. et al. "Safety Screens : Using a hypercomposite powder of thin-layer silica-coated zinc oxide in sunscreen . . . " Global Cosmetic Industry Feb. 2001: 32. Business Insights: Global. Web. Apr. 18, 2018.
Janjua N.R. et al. "Systemic absorption of the sunscreens benzophenone-3, octyl-methoxycinnamate, and 3-(4-methyl-benzylidene) camphor after whole-body topical application . . . " J. Invest. Dermatol. Jul. 2004; vol. 123, pp. 57-61.
Janjua, N.R. et al. "Sunscreens in human plasma and urine after repeated whole-body topical application." J Eur Acad. Dermatol. Venereol. vol. 22, No. 4, pp. 456-461 (2008). Epub Jan. 23, 2008.
Jimenez Reinosa, J. "Enhancement of UV absorption behavior in ZnO—TiO2 composites." Boletin de la Sociedad Espanola de Ceramica y Vidrio. 55 (2016): 55-62. Published Feb. 8, 2016.
Korzhinsky, M.A. et al. "Native Al and Si Formation." Institute of Experimental Mineralogy, Russian Academy of Sciences. Nature, vol. 375, p. 544. Jun. 15, 1995.
Kumar, P. et al. "Patent review on photostability enhancement of avobenzone and its formulations." Recent Pat Drug Deliv Formul. vol. 9, No. 2, pp. 121-128 (2015). Published Jul. 31, 2015.
Antaria Limited. "ZinClear XP (Zinc Oxide Powder)." Jun. 1, 2016.
Lionetti, N. "The New Sunscreens among Formulation Strategy, Stability Issues, Changing Norms, Safety and Efficacy Evaluations." Cosmetics 2017, 4, 15; doi: 10.3390/cosmetics4020015. Published May 16, 2017.
Non-Final Office Action on Feb. 20, 2019 for U.S. Appl. No. 15/934,312 (LCS18121USVAZ).
Final Office Action on Mar. 22, 2023 for U.S. Appl. No. 15/934,312 (LCS18121USVAZ).
Lohani, A. "Nanotechnology-Based Cosmeceuticals." Review Article. Hindawi Publishing Corporation. ISRN Dermatology. vol. 2014, Article ID 843687, 14 pages. Published May 22, 2014.
CeraVe. "Sunscreen Body Lotion SPF 50." https://incidecoder.com/products/cerave-sunscreen-body-lotion-spf-50; https://www.heb.com/product-detail/cerave-sunscreen-body-lotion-spf-50/1698233.

(56) References Cited

OTHER PUBLICATIONS

Lowe, N. "An overview of ultraviolet radiation, sunscreens, and photo-induced dermatoses." Dermatol Clin. Jan. 2006; 24(1): 9-17. doi: 10.1016/j.det.2005.08.001.
Lu, P.J. "Characterization of titanium dioxide and zinc oxide nanoparticles in sunscreen powder by comparing different measurements methods." Journal of Food and Drug Analysis. Published Feb. 15, 2018. pp. 1192-1200.
Mwangi et al. "Sunscreen products: Rationale for use, formulation development and regulatory considerations." Saudi Pharm J. Nov. 2019; 27(7): 1009-1018. doi: 10.1016/j.jsps.2019.08.003. Epub Aug. 16, 2019.
Office of Environmental Health Hazard Assessment, California EPA. "Proposition 65 of Safe Drinking Water and Toxic Enforcement Act of 1986." Jun. 2012.
DOW Personal Care. "Sunspheres Hollow Sphere Technology: An SPF Booster for More Aesthetically Pleasing Formulations." Feb. 22, 2007.
Dow Personal Care. "SunSpheres SPF Boosters: Hollow Sphere Technology for More Aesthetically-Pleasing Formulations at Higher SPF." Mar. 2, 2016. p. 4.
Dow Personal Care. "SunSpheres SPF Booster in Daily Wear Applications: Achieve Higher SPF and More Aesthetically-Pleasing Daily Moisturizer and Color Cosmetic Formulations with SunSpheres SPF Boosters." Mar. 2, 2016; Revised Jun. 10, 2019. p. 2.
Bionap S.r.l. "Olea HT-10." Olea Europea (Olive) Fruit Extract (and) Maltodextrin. Personal Care & Cosmetics. Accessed on Jul. 4, 2023.
Kobo Products. "KSL-199A: Elegant W/O White Sunscreen Lotion with Composite ACT-50." Aug. 2011.
Kobo Products. "Formulary: PCHi 2016." Aug. 2016.
Rajabi, L. et al. "Acetophenones with selective antimycobacterial activity." Letters in Applied Microbiology, vol. 40, Is. 3, pp. 212-217. https://doi.org/10.1111/j.1472-765X.2005.01657.x. First published Jan. 26, 2005.
Official Journal of the European Union. "Commission Recommendation of Sep. 22, 2006 on the fficacy of sunscreen products and the claims made relating thereto." 2006/647/EC. Broad Spectrum Sunscreen.
Rincon-Fontan, M. "Design and characterization of greener sunscreen formulations based on mica powder and biosurfactant extract." Powder Technology 327 (2018): 442-448. Published Jan. 5, 2018.
Rodrigues, N.D.N. "Photophysics of the sunscreen ingredient menthyl anthranilate and its precursor methyl anthranilate." Journal of Photochemistry and Photobiology A: Chemistry 353 (2018) 376-384. Published Dec. 1, 2017.
Access Ingredients. "Hectorite Technologies." Sunjin Beauty Science. May 2020, Version 3.5. Powerpoint, 2019.
Shao, Y. "Formulating mineral sunscreens for people of color." New York Society of Cosmetic Chemists. Jan. 28, 2021. https://nyscc.org/blog/formulating-mineral-sunscreens-for-people-of-color/.
Supelco. "Niacinamide PHR1033 Safety Data Sheet." Millipore Sigma. Analytical Reference Materials for the Pharma Industry. Version 6.8. 9 pages. Print date Jul. 1, 2023.
Sinerga. "Feniol, Phenethyl Alcohol (and) Caprylyl Glycol." Prospector. https://www.ulprospector.com/en/na/PersonalCare/Detail/12615/356929/Feniol. Accessed on Jul. 4, 2023.
Sinerga Skin Evolution. "Ewocream W/O skin shield." Varese, Italy. Accessed Jul. 4, 2023.
Smaoui, S. "Development and stability studies of sunscreen cream formulations containing three photo-protective filters." King Saud University. Arabian Journal of Chemistry (2017) 10, S1216-S1222. Published Mar. 14, 2013.
Science Daily, Science News. American Physical Society. "Photonic Crystal Sunscreen For Sea Scum." Sep. 19, 2006. http://www.sciencedaily.com/releases/2006/09/060918202844.htm.
Vigon. "SymRepair 100: Product Specification and Safety Data Sheet." Effective Date: Feb. 3, 2017.
Mayo Clinic Staff. "Coenzyme Q10 (CoQ10) Overview." Nov. 10, 2020. https://www.mayoclinic.org/drugs-supplements-coenzyme-q10/art-20362602.
Jungbunzlauer. "Citrofol AI and Citrofol BI Technical Datasheet." Universal Selector. Last edited Dec. 19, 2022.
Aveeno. "Positively Mineral Sensitive Skin Sunscreen Broad Spectrum SPF 50." NDC 69968-0395. Accessed on Jul. 4, 2023.
Neutrogena. "Sensitive Skin Sunscreen Lotion Broad Spectrum SPF 60+." Marketed Feb. 2017. Now discontinued. Https://www.neutrogena.com/products/sun/sensitive-skin-sunscreen-lotion-broad-spectrum-spf-60/6847260.html.
SkinCeuticals. "Physical Fusion UV Defense Broad Spectrum SPF 50." NDC 49967-077. Marketed Jan. 1, 2011. https://www.skinceuticals.com/skincare/sunscreens/physical-fusion-uv-defense-spf-50/S54.html#tab=key-ingredients.
Wang, J. "Reducing the Photocatalytic Activity of Zinc Oxide Quantum Dots by Surface Modification." Deakin University. J. Am. Ceram. Soc., 92 [9] 2083-2088 (2009). Published Apr. 5, 2009. doi: 10.1111/j.1551-2916.2009.03142.x.
Wang, S.Q. "Comparison of ultraviolet A light protection standards in the United States and European Union . . . " Journal of the American Academy of Dermatology. vol. 77, Issue 1, Jul. 2017, pp. 42-47. Published Feb. 24, 2017.
Non-Final Office Action dated Oct. 24, 2024 in U.S. Appl. No. 18/661,660 (LCS19371USIBI).

* cited by examiner

BROAD-SPECTRUM, MINERAL, PHOTOPROTECTIVE COMPOSITIONS

RELATED APPLICATIONS/PRIORITY

This patent application is a continuation of and claims priority to presently co-pending U.S. patent application Ser. No. 15/934,312, filed Mar. 23, 2018, entitled "Broad-Spectrum, Mineral, Photoprotective Compositions. This application claims the benefit of priority to, and incorporates by reference the entirety of, the above-referenced priority application.

FIELD OF THE INVENTION

Topical compositions that provide broad-spectrum (defined below) photoprotection across the ultraviolet radiation spectrum (from 280-400 nm).

BACKGROUND OF THE INVENTION

The scientific literature and media have raised health concerns (possible carcinogenicity and endocrine disruption) and other concerns (instability) with respect to certain "chemical" sunscreen filters (also known in the art as "organic" sunscreen filters, defined below).

Avobenzone, the most common organic sunscreen in broad-spectrum chemical sunscreen formulations, is known to undergo rapid photochemical degradation when exposed to ultraviolet radiation and is, therefore, considered "unstable." See, e.g., Kumar P et al., "Patent review on photostability enhancement of avobenzone and its formulations." Recent Pat Drug Deliv Formul. Vol. 9, No. 2, pp. 121-8 (2015); Afonso, S. et al. "Photodegradation of avobenzone: stabilization effect of antioxidants" J Photochem Photobiol B. Vol. 140, pp. 36-40 (2014); Beasley, D G et al., "Characterization of the UVA protection provided by avobenzone, zinc oxide, and titanium dioxide in broad-spectrum sunscreen products." Am J Clin Dermatol Vol. 11, No. 6, pp. 413-21 (2010).

Benzophenone-3, also known as oxybenzone, not only absorbs UVB and short UVA rays, but also prevents the degradation of other chemical sunscreens when exposed to UVR. In a podium presentation at the September 2007 Sunscreen Symposium organized by the Florida Chapter of the U.S. Society of Cosmetic Chemists, Craig Bonda reported that oxybenzone quenches avobenzone fluorescence, reducing the flow of singlet excited state energy to the triplet-excited state, and thereby decreasing the potential for chemical reactions that would photodegrade avobenzone.

Health concerns have, however, been raised about the potential adverse health effects from dermal absorption of benzophenone-3. In June 2012, the Office of Environmental Health Hazard Assessment (OEHHA) within the California Environmental Protection Agency added benzophenone-3 to the list of chemicals known to the State of California to cause cancer for purposes of the Safe Drinking Water and Toxic Enforcement Act of 1986 (Proposition 65).

Another commonly-used ingredient to stabilize avobenzone is the UV-B organic sunscreen filter, octocrylene. Health concerns have also been raised with respect to octocrylene. In 2010, in an article entitled "Octocrylene, an emerging photoallergen" published in Archives of Dermatology [Vol. 146, No. 7, pp. at pages 753-757 (2010)], Avenel-Audran M et al. reported that octocrylene appears to be strong allergen leading to contact dermatitis in children and mostly photoallergic contact dermatitis (in particular, in adults with a history of photoallergy from ketoprofen). See also, de Groot, AC and DW Roberts, "Contact and photocontact allergy to octocrylene: a review." Contact Dermatitis, Vol. 70, pp. 193-204. (2014).

The Environmental Working Group has raised health concerns regarding several organic sunscreen filters. See ewg.org/sunscreen/report/the-trouble-with-sunscreen-chemicals/, citing two publications (among others) by Janjua N R, et al.: Janjua N R, et al. "Systemic absorption of the sunscreens benzophenone-3, octyl-methoxycinnamate, and 3-(4-methyl-benzylidene) camphor after whole-body topical application and reproductive hormone levels in humans." J. Invest. Dermatol. Vol. 123, pp. 57-61 (2004); Janjua N R, et al. "Sunscreens in human plasma and urine after repeated whole-body topical application." J Eur Acad. Dermatol. Venereal. Vol. 22, No. 4, pp. 456-461 (2008).

Physical sunscreen filters (most commonly zinc oxide and titanium dioxide), while not raising health concerns of the type associated with organic/chemical sunscreen filters (as discussed above), nonetheless pose challenges both in terms of formulation and aesthetics. Achieving high levels of UVR photoprotection (e.g., SPF of at least 30, which can be described as providing "high protection against sunburn and tanning" under current US Food and Drug Administration regulations) with inorganic sunscreen formulations requires high loadings of physical sunscreen filters. Formulations with high particle loadings can become unstable, including agglomeration and settling of particles. In addition, physical sunscreen products with high SPF (greater than 30; and, especially, greater than 50) may be difficult to apply (spread, rub-in) and/or may be perceived as lacking cosmetic elegance (in terms of feel and/or appearance). Use of zinc oxide, particularly, at higher concentrations, is known to leave a white, pasty residue on the skin.

There has been, and remains, a need for sunscreen formulations that do not contain organic sunscreen actives, have an SPF of at least 30, and preferably at least 50, provide broad-spectrum UVR protection, and are cosmetically elegant—not oily, not tacky, leave no visible whitening on Fitzpatrick Skin Type I-IV, and are easily applied to the skin (spread). Those needs are met by the compositions of the present invention.

It is well-known in the art of formulating topical products (for personal care, cosmetic, skin care, and dermatologic applications) that achieving a stable emulsion formulation—one in which (i) a discontinuous inner phase is homogenously dispersed into a continuous external phase, and does not separate into two phases, and (ii) in which particles are and remain dispersed and do not settle—is difficult to accomplish with a single surfactant. Consequently, such formulations typically require at least two surfactants. But it is also known in the dermatologic arts that surfactants can have negative effects—both on the user and on the formulation itself. Many surfactants are known to be irritating. Surfactants can also interact with, and reduce, the activity of certain "anti-aging" ingredients (for example, by denaturing peptides). Moreover, surfactants can interact with film-forming polymers, thereby reducing water-resistant properties, which are highly desirable in sunscreens.

There has been, and remains, a need for emulsion sunscreen formulations that are stable, have a high level of water resistance (preferably 80 minutes in accordance with standards set out in Section 352.76 of Title 21 of the U.S. Code of Federal Regulations). These needs are also met by the compositions of the present invention.

SUMMARY OF THE INVENTION

Disclosed are broad-spectrum mineral sunscreen compositions in the form of water-in-oil (W/O) emulsions that, upon application to skin classified as Fitzpatrick Skin Types I-IV (as described in Appendix A), leave little or no visible deposition of a white "pasty" residue.

Sunscreen compositions of the present invention (a) provide broad-spectrum protection from ultraviolet radiation ("UVR") and have a sun protection factor (SPF) of at least 30, preferably at least 50, and (b) are water resistant, preferably for 80 minutes, (c) are not visibly non-whitening on Fitzpatrick Skin Types I-IV and (d) do not contain an organic sunscreen filter, and consist essentially of:

(i) two photoprotective metal oxides that block, reflect, refract or otherwise attenuate ultraviolet radiation: at least one zinc oxide particle, preferably uncoated; at least one titanium dioxide particle, preferably coated; and, optionally, one or more other metal oxides (that block, reflect, refract or otherwise attenuate visible, infrared or ultraviolet radiation);
(ii) two siliceous compounds
(a) an amorphous silica, preferably an amorphous spherical silica, and
(b) a mixture of diatomaceous algae comprising at least two, preferably three, and still more preferably all four of *Fragilaria zeilleri, Gomphonema angustatum, Navicula radiosa*, and *Cyclotella andancensis;*
(iii) two film-forming polymers, preferably copolymers of dimethicone and
(a) bis-vinyl dimethicone and
(b) acrylates
(iv) two silicone compounds, one silicone wax, (preferably cetyl dimethicone) and one silicone fluid (preferably selected from the group of dimethicone and phenyl trimethicone).

The inventive broad-spectrum sunscreen W/O emulsions of the present invention preferably contain a single emulsifier that (a) has a hydrophilic-lipophilic balance in the range of 3.0 to 8.0, more preferably 3.0 to 5.0 (b) does not contain polyethylene glycol and (c) is an ester formed with polyglycerin, preferably containing 3-6 glycerin units. It is surprising and unexpected to achieve a stable emulsion (i.e., one that does not separate into oil and water phases after storage at an elevated temperature of 50° C. for one month or 40° C. for three months) with only a single emulsifier.

Surprisingly and unexpectedly, the synergistic combination of an amorphous spherical silica and a mixture of diatomaceous algae comprising at least two, preferably three, and still more preferably all four of *Fragilaria zeilleri, Gomphonema angustatum, Navicula radiosa*, and *Cyclotella andancensis* in further combination with zinc oxide and titanium dioxide provides a sun protection factor of at least 50, with a critical wavelength of greater than about 375, without visible skin whitening on Fitzpatrick Skin Types I-IV.

The compositions of the invention also provide one, preferably several, cosmetic skin benefits including (a) reducing the appearance of fine lines/wrinkles, (b) improving skin barrier function (i.e., by reducing the rate/extent of trans-epidermal water loss), (c) making the skin feel smoother, more supple and softer, (d) creating the appearance of more even skin tone (reducing dyschromia) and/or (e) imparting "glow"/radiance (also described in the art as "brightness").

DEFINITIONS

"Organic Sunscreen" means small molecule organic chemical sunscreen molecules (also known in the art as 'active ingredients") that absorb UVR, and include sunscreen active ingredients that are generally recognized as safe and effective and are approved for over-the-counter use by the U.S. Food and Drug Administration ("FDA")—namely, avobenzone; cinoxate; dioxybenzone; ecamsule; homosalate; menthyl anthranilate; octocrylene; octyl methoxycinnamate; octyl salicylate; oxybenzone; p-aminobenzoic acid; padimate o; phenylbenzimidazole sulfonic acid; sulisobenzone; and trolamine salicylate. Organic sunscreens also include active ingredients approved by regulatory agencies outside the United States, but not currently approved by the FDA, including, 4-methylbenzylidene camphor, amiloxate, benzophenone-9, Mexoryl® XL, Neo Heliopan® AP, Parsol® SLX, Tinosorb® A2B, Tinosorb® M, Tinosorb® S, Uvasorb® HEB, Uvinul® A Plus, and Uvinul® T 150.

"Photoprotective metal oxide" means a particle that physically blocks ultraviolet, visible and/or infrared light, and thereby protects the skin, and reduces environmentally-caused damage which can manifest as fine lines, wrinkles, uneven pigmentation (dyschromia), loss of elasticity or firmness, increased dryness, reduced skin moisture, and loss of softness/suppleness.

"Water-in-oil emulsion" or "W/O emulsion" means an internal water phase dispersed in an external non-aqueous phase comprised of hydrophobic materials including oils, esters, and silicones. W/O emulsions can also be understood to include water-in-silicone emulsions.

"Broad-spectrum" refers to a level of protection from UVR provided by wearing a sunscreen that has a minimum critical wavelength of 370 nm and a sun protection factor (SPF) value of 15 or higher.

"Critical wavelength" is the wavelength for which the section under the integrated optical density curve starting at 290 nm is equal to 90 percent of the integrated section between 290 nm to 400 nm. Standards and test methods for determining "broad-spectrum" protection from UVR are set out in the final Sunscreen Monograph promulgated by the FDA on Jun. 17, 2011. See "Labeling and Effectiveness Testing; Sunscreen Drug Products for Over-the-Counter Human Use" published at Volume 76 of the Federal Register starting at page 35620, the disclosure of which is incorporated herein by reference.

Hydrophilic-lipophilic balance ("HLB") is a measure of the degree to which a surfactant is hydrophilic or lipophilic. HLB may be calculated in accordance with the methods published by Griffin in the Journal of the Society of Cosmetic Chemists: "Classification of Surface-Active Agents by 'HLB", J. Soc. Cosm. Chem., Vol. 1, No. 5, pp. 311-26; "Calculation of HLB Values of Non-ionic Surfactants" J. Soc. Cosm. Chem., Vol. 5, No. 4, pp. 249-56.

"One or more" means at least one and thus includes individual components as well as mixtures/combinations.

Compositions of the present invention consist essentially of, and consist of, the ingredients described hereinbelow, as well as additional (optional) ingredients known to the skilled artisan to provide features or benefits useful in providing protection from UVR (as well as UVR and infrared radiation) and also providing cosmetic/aesthetic benefits that include, but are not limited to, reducing the appearance of fine lines/wrinkles, improving skin barrier function (by reducing the rate/extent of trans-epidermal water loss), making the skin feel smoother/more supple/softer, creating the appearance of more even skin tone (reducing dyschromia) and/or "slow"/radiance (also described in the art as "brightness").

A basic and novel characteristic of the inventive broad-spectrum photoprotective compositions of the present invention is the absence of organic sunscreens. Accordingly, in describing and claiming such compositions as "consisting essentially of (a) two photoprotective metal oxides that block, reflect, refract or otherwise attenuate ultraviolet radiation . . . " it is meant that: zinc oxide (preferably uncoated) and titanium dioxide (preferably coated) are both essential required component ingredients; other metal oxides that block, reflect, refract or otherwise attenuate visible, infrared or ultraviolet radiation, including cerium oxide, aluminum oxide, and iron oxides, may be component ingredients; but organic sunscreens are not component ingredients.

Numbers used in describing quantities of ingredients and/or reaction conditions are to be understood as being modified in all instances by the term "about."

Unless otherwise indicated, percentages, parts and ratios are to be understood as based upon the total weight of the composition.

Numerical ranges are meant to include numbers within the recited range, and combinations of subranges between, the given ranges. For example, a range from 1-5, includes 1, 2, 3, 4 and 5, as well as subranges such as 2-5, 3-5, 2-3, 2-4, 1-4, etc.

"At least one" means one or more, and also includes individual components as well as mixtures/combinations.

"Cosmetically acceptable" (for example, "cosmetically acceptable carrier") means compatible with a keratinous substrate.

The disclosures of US granted patents and US pre-grant patent publications are incorporated, in pertinent, by reference.

Photoprotective Metal Oxide Particles

Broad-spectrum photoprotective compositions of the present invention contain at least two photoprotective metal oxides—zinc oxide (ZnO) and titanium dioxide ($TiO_2$).

$TiO_2$ can be amorphous or crystalline in the rutile and/or anatase form. Preferably 95% or more of the $TiO_2$ is in the rutile form.

ZnO and $TiO_2$ can be, and in certain preferred embodiments, are coated. Coating is done by methods known in the art. By way of non-limiting example, starting with an aqueous pigment particle suspension, metal salts are added in dissolved form as so-called precursor compounds. Alkaline or acid substances are then used to set the pH value of the suspension in such a way that the precursor compounds are precipitated in the form of oxides, hydroxides, etc. Methods for modifying and hydrophobizing the surface of $TiO_2$ and ZnO are further disclosed, for example, in U.S. Pat. Nos. 5,565,591 and 5,486,631, both now expired.

Preferred, but non-limiting examples of materials that can be used to coat ZnO and $TiO_2$ are silica, alumina, aluminum hydroxide, aluminum stearate, triethoxycaprylsilane, stearic acid, caprylic/capric triglyceride, lecithin, and methicone.

Silica is the inorganic oxide that conforms to the formula $SiO_2$.

Alumina is an inorganic compound that conforms to the structure $Al_2O_3$.

Aluminum hydroxide is an inorganic compound that conforms to the structure $Al(OH)_3 \cdot xH_2O$.

Aluminum stearate is the aluminum salt of stearic acid that conforms to the formula: $CH_3(CH_2)_{16}COOAl(OH))_2$.

Triethoxycaprylylsilane is a siloxane ether that conforms to the formula:

$(CH_3CH_2O)_3Si(CH_2)_7CH_3$. Stearic acid is a fatty acid that conforms to the structure. $(CH_3CH_2)_{16}COOH$.

Caprylic/Capric triglyceride is the mixed triester of glycerin and caprylic and capric acids.

Methicone is a linear monomethyl polysiloxane that conforms generally to the formula:

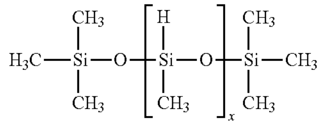

Photoprotective metal oxides may also be a mixture of $C_{12}$ to $C_{30}$ fatty alcohols and $C_6$ to $C_{12}$ aliphatic acids, as described in U.S. Pat. No. 9,517,190.

$TiO_2$ useful in W/O emulsion compositions of the present invention may be commercially available in a mixture that is a "binary combination"—namely, $TiO_2$ and a second ingredient selected from the group of: dimethicone; isopropyl titanium triisostearate; methicone; polymethyl methacrylate; polyphosphorylcholine glycol acrylate; silica; simethicone; -stearic acid; and triethoxycaprylylsilane.

$TiO_2$ useful in broad-spectrum sunscreen compositions of the present invention may also be part of a tripartite combination (i.e., $TiO_2$ and a second ingredient, and a third ingredient).

In certain embodiments, $TiO_2$ and Alumina (as a second ingredient) are combined with a third ingredient selected from the group of: glycerin; jojoba esters; methicone; silica; and stearic acid.

In other embodiments, $TiO_2$ and aluminum hydroxide (as a second ingredient) are combined with a third ingredient selected from the group of: hydrogen dimethicone; isostearic acid; and stearic acid.

In further embodiments, $TiO_2$ and silica (as a second ingredient) are combined with a third ingredient selected from the group of: Helianthusannuus (sunflower) seed oil; dimethicone; stearic acid; jojoba esters; lauroyl lysine; sodium polyacrylate; and triethoxycaprylylsilane.

In still further embodiments, $TiO_2$ and polyhydroxystearic acid (as a second ingredient) are combined with a third ingredient selected from the group of: bisabolol; squalane; and jojoba esters.

$TiO_2$ and caprylic/capric triglyceride may be combined with alumina, and polyhydroxystearic acid and one of: aluminum stearate; methicone; stearic acid; silica $TiO_2$ and caprylic/capric triglyceride may be combined with aluminum hydroxide, polyhydroxystearic acid and/or stearic acid.

$TiO_2$ may be combined with $C_{12-15}$ alkyl benzoate, polyolyhydroxystearic acid, and, optionally, but preferably alumina, in further combination with one of: methicone; cyclomethicone; aluminum stearate; stearic acid, and silica.

$TiO_2$ may also be combined with $C_{12-15}$ alkyl benzoate in further combination with

*Argania spinosa* kernel oil (and) alumina (and) methicone (and) tocopheryl acetate Dimethicone (and) polyhydroxystearic acid (and) silica Polyglyceryl-3 polyricinoleate (and) silica (and) stearic acid (and) aminopropyl-triethoxysilane Stearic acid (and) aluminum hydroxide (and) polyhydroxystearic acid $TiO_2$ may be combined with aluminum hydroxide in further combination with Acrylates copolymer (and) hydrated silica (and) algin Butyloctyl salicylate (and) isostearic acid (and) $C_{12-15}$ alkyl benzoate (and) stearic acid $C_{12-15}$ alkyl benzoate (and) stearic acid (and) polyhydroxystearic acid Caprylic/Capric triglyceride (and) stearic acid in further combination with (a) sorbitan olivate or (b) polyhydroxystearic acid Hydrogen dimethicone Hydrated silica (and) polyphosphorylcholine glycol acrylate Stearic acid or isostearic acid Polydimethylsiloxyethyl hexyl dimethicone (and) PEG-9 polydimethylsiloxyethyl dimethicone Polyglyceryl-4 isostearate (and) cetyl PEG/PPG-10/1 dimethicone (and) hexyl laurate (and) isostearic acid

*Simmondsia chinensis* (jojoba) seed oil (and) isostearic (and) polyhydroxystearic acid

*Simmondsia chinensis* (jojoba) seed oil (and) Polyhydroxystearic acid (and) jojoba esters Non-limiting examples of "coated" $TiO_2$ suitable for use in broad-spectrum sunscreen compositions of the present invention include the following:

Sunsil® Tin50 from Sunjin Chemical Co. Ltd.: $TiO_2$ coated with silica, with a ratio of silica to $TiO_2$ of about 55:45.

Titanium dioxide (at least 78%; typically about 83%) coated with aluminum hydroxide (about 9%) (and) stearic acid (about 8%), available from Tayca Corp. (Osaka, Japan) under the tradename MT-100TV.

Titanium dioxide (74%) coated with silica (11%), aluminum hydroxide (9%), and alginic acid (5%), available from Tayca Corp. as MT100-AQ.

Titanium dioxide (75-82%) coated with silica (13-20%) available from Merck KgaA/EMD Chemicals (Darmstadt, Germany) under the tradename Eusolex® T-AVO.

SiClone® TD-150 (from Presperse Corp., Somerset, New Jersey) about 40% titanium dioxide with an inner coating of aluminum hydroxide and an outer coating of isostearic acid.

$TiO_2$ may be used in broad-spectrum sunscreen compositions of the present invention in one of the following combinations:

(a) Boron nitride (and) dimethicone (and) isododecane (and) ethylene/VA copolymer (b) Butylene glycol (and) caprylyl glycol (and) oleth-10 (and) phenoxyethanol (and) polysorbate 60 (and) silica (c) Butyloctyl salicylate (and) polyhydroxystearic acid (and) dimethicone (and) hydrogen dimethicone (d) Caprylic/capric triglyceride (and) stearic acid (and) isostearic acid (and) polyhydroxystearic acid (and) polyglyceryl-3 polyricinoleate (and) lecithin (e) Cyclomethicone (and) bis-PEG/PPG-14/14 dimethicone (and) aluminum stearate (f) Cyclopentasiloxane (and) dimethicone (and) PEG-10 dimethicone (and) silica (g) Cyclopentasiloxane (and) PEG-10 dimethicone (and) methicone (h) Ethylene/acrylic acid copolymer (and) aluminum stearate (i) Ethylhexyl palmitate (and) polyhydroxystearic acid (and) silica (j) Glycerin (and) sodium polyacrylate (and) tetrasodium EDTA (and) silica (and) sodium polyphosphate (k) Hydrogenated polydecene (and) polyhydroxystearic acid (and) one of: dimethicone; stearic acid; or triethoxycaprylylsilane (l) Isododecane (and) polyhydroxystearic acid (and) methicone (m) Isohexadecane (and) triethylhexanoin (and) aluminum stearate (and) polyhydroxystearic acid (n) Isononyl isononanoate (and) methicone (and) polyhydroxystearic acid (o) Isopropyl myristate (and) polyhydroxystearic acid (and) silica (p) Isopropyl titanium triisostearate (and) triethoxysilylethyl polydimethylsiloxyethyl dimethicone (q) Methyl trimethicone (and) hydrogen dimethicone (and) lauryl PEG-9 polydimethylsiloxyethyl dimethicone (r) Methyl trimethicone (and) PEG-10 dimethicone (and) methicone (s) Mica (and) dimethicone (and) isododecane (and) ethylene/VA copolymer (and) stearic acid (t) Octyldodecyl myristate (and) alumina (and) polyhydroxystearic acid (and) methicone (u) Phenyl trimethicone (and) hexyl laurate (and) stearic acid (and) polyhydroxystearic acid (v) Polyglyceryl-2 caprate (and) sucrose stearate (and) *Simmondsia chinensis* (jojoba) seed oil (and) stearic acid (and) glyceryl caprylate (and) squalane (w) *Simmondsia chinensis* (jojoba) seed oil (and) aluminum hydroxide (and) polyhydroxystearic acid (and) one of isostearic acid or jojoba esters (x) Acrylates copolymer (and) hydrated silica (and) (a) algin (and) aluminum hydroxide or (b) polyphosphorylcholine glycol acrylate (y) Butyloctyl salicylate (and) aluminum hydroxide (and) isostearic acid (and) $C_{12}$-15 alkyl benzoate (and) stearic acid (z) $C_{12-15}$ alkyl benzoate (and) polyglyceryl-2 dipolyhydroxystearate (and) silica (and) dimethicone (aa) Caprylic/capric triglyceride (and) sorbitan olivate (and) stearic acid (and) aluminum hydroxide (bb) Caprylyl methicone (and) cyclopentasiloxane (and) $C_{12-15}$ alkyl benzoate (and) alumina (and) polyhydroxystearic acid (and) triethoxysilylethyl polydimethylsiloxyethyl hexyl dimethicone (and) PEG-9 polydimethylsiloxyethyl dimethicone (cc) Hydrated silica (and) hydrogen dimethicone and (a) aluminum hydroxide (or) hydrogen dimethicone (dd) Isododecane (and) alumina (and) methicone (and) polyhydroxystearic acid (ee) Isododecane (and) polyglyceryl-4 isostearate (and) cetyl PEG/PPG-10/1 dimethicone (and) hexyl laurate (and) aluminum hydroxide (and) isostearic acid (ff) Isononyl isononanoate (and) polyhydroxystearic acid (and) hydrogen dimethicone (and) dimethicone One preferred form of titanium dioxide suitable for use in broad-spectrum sunscreen compositions of the present invention is Tinoply E50C (manufactured by Chemland, Co., Ltd., Seoul, Korea) a mixture of caprylic/capric triglyceride, titanium dioxide, alumina, stearic acid, and polyhydroxystearic acid. More particularly, in Tinoply E50C (a) caprylic/capric triglyceride is present at a concentration of 47.0±2.5%, (b) titanium dioxide is present at a concentration of 39.0±2.5%, (c) alumina is present at a concentration of 6.0±2.5%, (d) stearic acid is present at a concentration 5.0±2.5%, and (e) polyhydroxystearic acid is present at a concentration of 3.0±0.5%.

Another preferred form of titanium dioxide suitable for use in broad-spectrum sunscreen compositions of the present invention is Tinoply E30C—a mixture of caprylic/capric triglyceride, titanium dioxide, silica, polyhydroxystearic acid, and methicone (also manufactured by Chemland, Co., Ltd.) in which (a) caprylic/capric triglyceride is present at a concentration of about 68.2±2.5%, (b) titanium dioxide is present at a concentration of at least about 24%, (c) silica is present at a concentration of 4.5±2.5%, (d) polyhydroxystearic acid is present at a concentration 1.8±0.5%, and (e) methicone at a concentration of 1.5±0.5%.

In certain especially preferred embodiments, the sunscreen does not include alumina.

Uncoated zinc oxide particles that can be used in compositions of the present invention are commercially available from numerous suppliers, including under the tradename Z-Cote® (BASF Care Creations, Florham Park, NJ). Examples of other suitable ZnO are disclosed, for example, in U.S. Pat. No. 8,545,891.

In preferred embodiments ZnO is non-whitening when applied to the skin and has an average particle size greater than about 100 nm (i.e., "non-nano"). Such materials are sometimes described in trade literature as "transparent". Historically, non-whitening, non-nano ZnO materials were marketed under the tradename ZinClear™ formerly sold by Antaria Limited (Welshpool, Australia). See US Pre-Grant Patent Application Publications 2010/0310871 and 2010/0316582, both abandoned.

In one particularly preferred embodiment, compositions of the present invention contain ZnO particles having an average particle size of greater than 100 nanometers. One such ZnO is ARGA-SUN ZnO CLR-P from Argan Co. (Northridge, California). According to Technical Data Sheets, ARGA-SUN ZnO CLR-P has a highly porous structure that is "infiltrated" (e.g., filled) with excipient, and an average particle size distribution of less than about 800 nanometers (measured using static laser scattering). Because the particles have a refractive index close to the excipient, a "significant increase in transparency" is achieved.

In preferred embodiments of the present invention, prior to mixing ZnO with $TiO_2$, ZnO is dispersed in polyhydroxystearic acid (PHSA), a polymer of hydroxystearic acid, which is commercially available under the tradename Dispersun DSP OL 300 from Innospec Performance Chemicals (Salisbury, NC). According to technical literature from Innospec, polyhydroxystearic acid increases UV absorption of sunscreens containing pigments by allowing higher concentrations of pigment to be used. Additionally, inclusion of polyhydroxystearic acid is described by Innospec as improving optical transparency and reducing whitening (when a finished formulation is applied to human skin).

In preferred embodiments, polyhydroxystearic acid is present at a concentration of from about 0.25 to 1.5%, preferably at least about 0.5%.

Different molecular weights of polyhydroxystearic acid may be used in broad-spectrum compositions of the present invention.

Optionally, but in certain preferred embodiments, one or more additional Photoprotective Metal Oxides selected from the group of iron oxides, zirconium oxide, bismuth oxychloride and cerium oxide are incorporated in broad-spectrum sunscreen compositions of the present invention.

In certain embodiments, $CeO_2$ is present in the broad-spectrum photoprotective compositions of the present invention at a concentration of from 0.1 to 2.0%, preferably about 0.25%.

One preferred form of cerium oxide is ARG-SPHERE NIR-1/15BA000—a combination of poly(methyl methacrylate), also known in the art as PMMA, cerium oxide ($CeO_2$), and aluminum oxide from Argan Co.

PMMA is a spherical ultra-fine texturizing powder, available in various sizes, used in powders to increase smoothness, fluidity and lubricity. It is a polymer of methyl methacrylate, has an empirical formula $C_5H_8O_2$)x and conforms to the following structure:

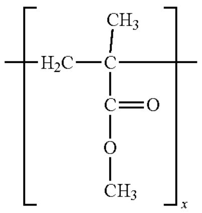

Iron oxides may be present in broad-spectrum photoprotective compositions of the present invention at a concentration of from about 1.0 to 7.0%, preferably from about 1.0 to 3.0%, and still more preferably from about 1.5 to 2.0%.

In tinted formulations (containing three or more iron oxides selected from the group of black iron oxide, red iron oxide, and yellow iron oxide), amorphous spherical silica is preferably present at a concentration of at least 2.0%.

In non-tinted formulations (not containing iron oxides), amorphous spherical silica is preferably present at a concentration of at least 2.5%.

In certain preferred embodiments, a mica, or a mica-like compound that imparts shimmer, glow, or reduces the appearance of skin imperfections, is added to the formulation.

One preferred, but non-limiting example, of a mica-like compound is synthetic fluorphlogopite, a synthetic mineral that conforms generally to the formula: $Mg_3K[AlF_2O(SiO_3)_3]$.

Siliceous Compounds

Broad-spectrum photoprotective compositions of the present invention contain two siliceous compounds—an amorphous silica and a mixture of diatomaceous algae, each described in detail below.

A first siliceous compound that is an essential ingredient of the broad-spectrum photoprotective compositions of the present invention is amorphous silica, also known in the art as amorphous silicon oxide hydrate. Preferably, the amorphous silica is a spherical, porous powder, still more preferably having a mean particle size ranging from about 6 microns to about 10 microns. One especially preferred amorphous spherical silica is Silisphere LS-8H available from Argan Co.

A second siliceous compound that is an essential ingredient of the broad-spectrum photoprotective compositions of the present invention is a mixture of diatomaceous algae—unicellular, photosynthetic microorganisms having a nanopatterned cell encasement made of amorphous biosilica, also known in the art as a "frustule", that creates a highly efficient light trapping mechanism. See J. Romann et al. "Wavelength and orientation dependent capture of light by diatom frustule nanostructures" (2015), published online at nature.com/articles/srep17403; X. Chen et al., "Numerical and experimental investigation of light trapping effect of nanostructured diatom frustules" (2015), published online at nature.com/articles/srep11977. See also J. Mishler et al, "Biomimetic Photonic Crystals based on Diatom Algae Frustules" presented at the March 2015 meeting of the American Phytopathological Society, Abstract #A4.004.

Amorphous silica, preferably amorphous spherical silica, is present in broad-spectrum photoprotective compositions of the present invention at a concentration of from about 0.5 to about 5.0%.

Plankton Glass Flower® (INCI Name: "Plankton Extract"), a combination of diatomaceous algal species, is commercially available from Odycea SAS (Lannion, France) and distributed in the United States by Argan Co. (Northridge, California). Technical data sheets and brochures describe Plankton Glass Flower as "algal photonic and porous silica crystals" or, alternatively, "planktonic material" sourced from the lakes in the volcanic region of Auvergne, France—namely, "siliceous fragments of freshwater algae species[,] mainly *Fragilaria zeilleri, Gomphonema angustatum, Navicula radiosa*, and *Cyclotella andancensis*"—that contains greater than about 75% silica. Plankton Glass Flower not only provides "UV-visible [light] attenuation due to both reflection and scattering" but also serves as an "oil absorber" and "pollutant scavenger which entraps . . . impurities [at the surface of the skin]."

One, or preferably a mixture of two or more, diatomaceous algal species having photonic and porous silica crystals and a silica content of at least about 75% is/are present in broad-spectrum photoprotective compositions of the present invention at a concentration of from about 0.1 to about 2.0%, preferably from about 0.25 to about 1.0%, and even more preferably at a concentration of at least about 0.5%.

Preferably the one or more diatomaceous algal species having photonic and porous silica crystals and a silica content of at least about 75% are selected from the group consisting of *Fragilaria zeilleri, Gomphonema angustatum, Navicula radiosa*, and *Cyclotella andancensis*.

In preferred embodiments of the present invention the ratio of (i) one or more diatomaceous algal species having photonic and porous silica crystals and a silica content of at least about 75% to (ii) amorphous silica, preferably spherical, porous silica, is from about 1:9 to about 1:3.

Total silica content in compositions of the present invention—silica found in (i) one or more diatomaceous algal species having photonic and porous silica crystals and a silica content of at least about 75% and (ii) amorphous silica, preferably amorphous, spherical silica—is preferably from about 1.0 to about 5.0%, more preferably from about 2.0 to about 4.0%.

In certain preferred embodiments that contain $CeO_2$, the ratio of (1) $CeO_2$ to (2) Plankton Glass Flower (as described above) to (3) amorphous silica is 1:2:8.

In some especially preferred embodiments of the present invention that are tinted with at least two iron oxides, the ratio of (i) one or more diatomaceous algal species having photonic and porous silica crystals and a silica content of at least about 75% to (ii) amorphous silica, preferably spherical, porous silica, is about 1:4.

In other especially preferred embodiments of the present invention that are not tinted (i.e., do not contain iron oxides), the ratio of (i) one or more diatomaceous algal species having photonic and porous silica crystals and a silica content of at least about 75% to (ii) amorphous silica, preferably spherical, porous silica, is about 1:5.

SPF Boosters

Broad-spectrum photoprotective compositions of the present invention contain at least one, preferably at least two, and still more preferably three SPF boosters selected from the group of styrene/acrylates copolymer, butyloctyl salicylate, and triethyl citrate (each as described below), and polyhydroxystearic acid (described above).

Styrene/acrylates copolymer is a polymer of styrene and a monomer consisting of acrylic acid, methacrylic acid or one of their simple esters. These hollow spheres are manufactured via emulsion polymerization, and are commercially available from Dow (Midland, Michigan) under the name SUNSPHERES® Powder. A February 2006 Technical Data Sheet (TDS) describes SUNSPHERES® as "rais[ing] UV protection over the whole UVA/UVB spectrum".

Butyloctyl salicylate (CAS No. 190085-41-7), commercially available as HallBrite® BHB from the Hallstar Company (Chicago, Illinois) and SunSolv® from Innospec Performance Chemicals (Salisbury, North Carolina) is a synthetically produced ester of salicylic acid and a branched $C_{12}$ alcohol, 2-butyloctanol. Butyloctyl salicylate, and its uses in topical formulations, are described in the following U.S. Pat. Nos. 5,783,173; 5,788,954; 5,849,273; and 6,350,894.

Triethyl citrate is the triester of ethyl alcohol and citric acid that conforms to the formula:

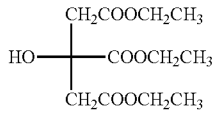

Surprisingly and unexpectedly, broad-spectrum photoprotective compositions of the present invention containing at least one, preferably at least two, and more preferably three of the above SPF boosters provide an SPF of at least 30, and, in preferred embodiments, an SPF of at least 50, without visible whitening on Skin Types I-IV under the Fitzpatrick Skin Type system of skin classification, described in Appendix A.

Water-In-Oil Emulsifier

In preferred embodiments of the present invention, the inventive broad-spectrum photoprotective composition contains a single emulsifier having a low HLB, by which is meant from about 3.0 to about 8.0, more preferably from about 3.0 to about 5.0, and still more preferably from about 3.5 to about 4.0.

Preferably, the low HLB W/O emulsifier is present at a concentration of from about 2.25% to about 6%, preferably at least about 2.5%, more preferably at least 5%.

One preferred, but non-limiting example, of a low HLB W/0 emulsifier is an ester formed with polyglycerin, preferably containing 3-6 glycerin units. These low HLB W/O emulsifiers are free of polyethylene glycol (i.e., are "PEG-Free"). Non-limiting examples of preferred low HLB W/O ester emulsifiers are polyglyceryl-3 oleate, polyglyceryl-3 ricinoleate, polyglyceryl-3 sesquiisostearate, polyglyceryl-3 polyricinolate, and polyglyceryl-4 oleate.

Polyglyceryl-3 oleate, polyglyceryl-3 ricinoleate, polyglyceryl-3 sesquiisostearate, and polyglyceryl-3 polyricinoleate are all esters formed from polyglycerin-3, a glycerin polymer containing 3 glycerin units.

Polyglyceryl-4 oleate is an ester of oleic acid and polyglycerin-4, a glycerin polymer containing 4 glycerin units.

Film-Forming Polymers and Silicone Compounds

Siloxanes, also known in the art as organo-substituted polysiloxanes, are linear or cyclic polymers of monomeric silicon/oxygen monomers, in which a polymeric backbone is made up of alternating silicon and oxygen atoms. The silicon atoms may carry a wide variety of substituents, which can be the same or different.

"Film-forming" ingredients are chemicals that produce a continuous film on skin.

Compositions of the present invention preferably have a water resistance of 80 minutes and are comprised of at least one, preferably at least two, film-forming polysiloxane polymers.

In particularly preferred embodiments, the two film-forming polymers are (i) bis-vinyl dimethicone/dimethicone copolymer, commercially available in combination with dimethicone or cetyl dimethicone and (ii) dimethicone (and) acrylates/dimethicone copolymer.

Bis-vinyl dimethicone/dimethicone copolymer is a copolymer of dimethicone end-blocked with vinyl dimethicone.

Dimethicone $(C_2H_6OSi)_xC_4HuSi$ is a mixture of fully methylated linear siloxane polymers end blocked with trimethylsiloxy units; it conforms generally to the formula:

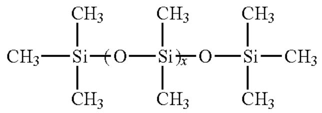

Vinyl dimethicone is a derivative of dimethicone in which some of the methyl groups are replaced with vinyl groups. The vinyl groups can occur at the ends of the siloxane chain may be pendant to the siloxane chain. It conforms generally to the formula:

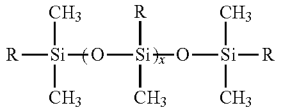

where R is a methyl or vinyl group, and at least one vinyl group is present.

Bis-vinyl dimethicone is a derivative of dimethicone in which one methyl group at each end of the siloxane chain is replaced with a vinyl group. It conforms generally to the formula:

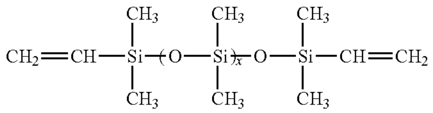

Cetyl dimethicone is a dimethyl siloxane polymer that conforms to the formula:

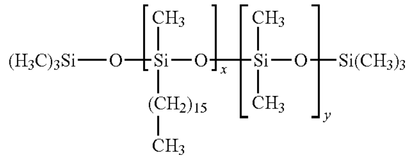

Acrylates/dimethicone copolymer is a copolymer of dimethicone and one or more monomers of acrylic acid, methacrylic acid or one of their simple esters.

In addition to the two dimethicone copolymer film formers (discussed immediately above), the broad-spectrum photoprotective compositions of the invention are comprised of at least two, preferably three silicone compounds selected from methicone, dimethicone, simethicone, cetyl dimethicone and phenyl trimethicone.

More preferably, a first silicone compound is a silicone wax (preferably cetyl dimethicone), and a second silicone compound is a silicone fluid (preferably selected from the group of methicone, dimethicone, simethicone, and phenyl trimethicone).

Methicone is a linear monomethyl polysiloxane that conforms generally to the formula:

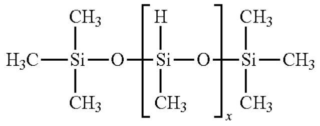

Simethicone is a mixture of dimethicone with an average chain length of 200 to 350 dimethylsiloxane units and silica.

Phenyl trimethicone is the siloxane polymer that conforms generally to the following formula, in which x is predominantly 1 to 3:

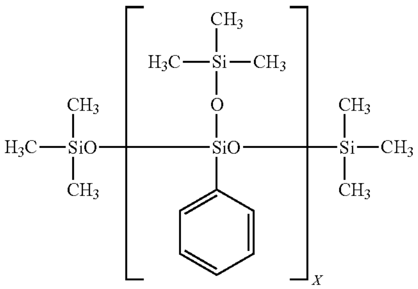

Phenyl trimethicone is preferably used in combination with (a) disteardimonium hectorite and (b) triethyl citrate. Disteardimonium hectorite is the reaction product (a) hectorite, one of the montmorillonite minerals that are the principal constituents of bentonite clay and (b) distearyldimonium chloride, a quaternary ammonium salt. Triethyl citrate is a triester of ethyl alcohol and citric acid. The above combination is commercially available as Bentone Gel PTM V from Elementis Specialities, Inc. (Hightstown, NJ) and functions as a non-surfactant dispersing agent, preventing syneresis and settling of photoprotective metal oxide particles.

In certain preferred embodiments, at least two dimethicones are included in the broad-spectrum photoprotective compositions of the invention: a first dimethicone having a lower kinematic viscosity in the range of 0.65 to 400 centistokes (cst), preferably about 50 cst;

and a second dimethicone having a higher kinematic viscosity in the range of 1,000 to 5,000 cst.

Dimethicone and cetyl dimethicone are preferably present in broad-spectrum photoprotective compositions of the invention at a concentration of from 1 about 5%; preferably less than about 4.5, still more preferably about 4.0.

Additional Ingredients

Broad-spectrum photoprotective compositions of the present invention preferably include one or several ingredients that (a) reduce visible redness (i.e., erythema) or inflammation (known in the art as anti-inflammatory) or act as an antioxidant (i.e., reduce oxidative damage; also known in the art as free radical quenchers), (b) reduce the appearance of the signs of skin aging, which can include fine lines, wrinkles, uneven pigmentation (dyschromia), loss of elasticity or firmness, increased dryness, reduced skin moisture, loss of softness/suppleness (collectively "anti-aging ingredients"), or (c) oil-absorbent powders. Non-limiting examples of antioxidants and anti-aging ingredients include: vitamins and derivatives thereof, preferably, ascorbic acid (vitamin C) and its salts; ascorbyl esters of fatty acids, ascorbic acid derivatives (e.g., magnesium ascorbyl phosphate, sodium ascorbyl phosphate, ascorbyl sorbate); tocopherol (vitamin E), tocopherol sorbate, tocopherol acetate, other esters of tocopherol; coenzyme Q10 (ubiquinone, ubiquinol) and its analogues, including without limitation, idebenone; bioflavonoids; amino acids; peptides, preferably comprised of two to ten amino acids, still more preferably lipidated peptides; superoxide dismutase; dipotassium glycyrrhizinate; tea extract or coffee extract; stem cells, including stem cell lysates; ceramides; as well as ingredients known in the art as humectants, moisturizers, skin-conditioning agents, skin soothing and/or healing agents.

Non-limiting examples of antioxidants/radical scavengers/moisturizing agents which may be topically delivered in the broad-spectrum photoprotective compositions of the present invention include: bisabolol; *Camellia sinensis* leaf extract; Capparis *spinosa* fruit extract; hydroxyacetophenone; *Olea europaea* (olive) fruit extract, preferably containing hydroxytyrosol (10% HPLC); *Opuntia ficus*-indica extract; *Polygonum* aviculare extract; *Zingiber officinale* root extract.

Preferred, but non-limiting examples of oil-absorbent powders include nylon-12 and polymethylsilsesquioxane.

Nylon-12 is a polyamide derived from 12-aminododecanoic acid and conforms generally to the formula:

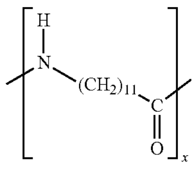

Polymethylsilsesquioxane is a polymer formed by the hydrolysis and condensation of methyltrimethoxysilane.

In certain embodiments, nylon-12 is combined with polymethyl methacrylate or polymethyl-silsesquioxane.

Certain embodiments of the present invention include ingredients that act as pollutant scavengers (i.e., entrap or reduce the negative effects of environmental particulate matter on the skin). By "negative effects on the skin" is meant collagen degradation, overproduction of melanin, and inflammation. Non-limiting examples of preferred pollutant scavengers include Plankton Glass® (described above) and benzylidene dimethoxydimethylindanone (available under the tradename SymUrban® from Symrise, Teterboro, NJ).

Compositions of the present invention preferably contain one or several ingredient(s) that absorb, attenuate or reduce negative effects on the skin caused by blue light and/or infrared radiation.

One non-limiting, preferred example of an ingredient that counters the effects of infrared radiation on the skin is a combination of PMMA, cerium oxide, aluminum oxide, available from Argan under the tradename ARG-NIR.

One non-limiting, preferred example of an ingredient that counters the effects of blue radiation on the skin is lutein, available as FloraGLO™ Lutein 5% Topical [carthamus tinctorius (safflower) seed oil (and) *tagetes erecta* flower extract] and FloraGLO™ Lutein 10% Topical [Water-dispersible granules of sucrose (and) tapioca starch (and) xanthophyll].

Sunless tanning agents, including but not limited to the alpha-MSH biomimetic peptide acethyl hexapeptide-1, may be added to the broad-spectrum photoprotective compositions of the present invention.

In certain preferred embodiments, broad-spectrum sunscreen compositions of the present invention contain an ingredient that reduces pigmentation induced by both infrared light and visible light (from 400-700 nm), preferably carnosine.

Carnosine (available from Symrise under the tradename Dragosine®) is heterocyclic amine that conforms to the formula:

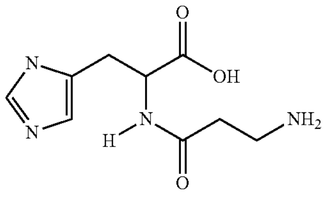 [SMILES: NCCC(=O)NC(Cc1cnc[nH]1)C(=O)O]

In certain preferred embodiments, carnosine is present at a concentration of from 0.01-0.2%.

Compositions of the present invention preferably do not contain any of the following: paraben, formaldehyde, chlorphenesin, and phenoxyethanol. Instead, as a preferred preservative system, compositions of the present invention have a synergistic combination of: hydroxyacetophenone (preferably at 0.5%); a mixture of 1,2 hexanediol (and) caprylyl glycol (preferably at a combined concentration of 0.5%); a mixture of bisabolol (and) *Zingiber officinale* (ginger) extract (preferably at a combined concentration of 0.1%). This synergistic combination passes the microbial enumeration test found in Chapter 61 of the US Pharmacopeia.

The invention is further defined by reference to the following examples. These examples are representative, and should not be construed to limit the scope of the invention.

| Phase | Ingredient(s) | SPF 30 | SPF 55 |
|---|---|---|---|
| A | Water | Q.S. | Q.S. |
| A | Glycerin 99.7%, USP | 0.25-1.00 | 0.25-1.00 |

-continued

| Phase | Ingredient(s) | SPF 30 | SPF 55 |
|---|---|---|---|
| A | Panthenol | 0.10-0.50 | 0.10-0.50 |
| A | Allantoin | 0.05-0.25 | 0.05-0.25 |
| A | 1,2 Hexanediol and Caprylyl Glycol | 0.10-1.00 | 0.10-1.00 |
| A | Hydroxyacetophenone | 0.10-1.00 | 0.10-1.00 |
| A | Sodium Chloride | 0.25-1.50 | 0.25-1.50 |
| A | Niacinamide | 0.10-3.00 | 0.10-3.00 |
| B | Butyl Octyl Salicylate | 15.0 | 12.5 |
| B | Squalane | 0.50-2.00 | 0.50-2.00 |
| B | Cetyl Dimethicone (and) Bis-Vinyl Dimethicone/Dimethicone Copolymer | 4.0 | 4.0 |
| B | Dimethicone (and) Bis-Vinyl Dimethicone/Dimethicone Copolymer | 4.0 | 4.0 |
| B | Styrene/Acrylates Copolymer (2.00-5.50) | 2.5 | 5.5 |
| B | Polyhydroxystearic Acid | 0.25-1.00 | 0.25-1.00 |
| B | Zinc Oxide | 5.0 | 10.00 |
| B | Iron Oxides | 1.5-2.0 | 0.0 |
| C | Phenyl Trimethicone, Disteardimonium Hectorite, (and) Triethyl Citrate | 1.50-3.00 | 1.50-3.00 |

-continued

| Phase | Ingredient(s) | SPF 30 | SPF 55 |
|---|---|---|---|
| C | Caprylic/Capric Triglyceride, Titanium Dioxide, Aluminum Hydroxide, Stearic Acid (and) Polyhydroxystearic Acid | 3.5 | 3.5 |
| C | Dimethicone (and) Acrylates/Dimethicone Copolymer | 1.00-3.00 | 1.00-3.00 |

Preferably, iron oxides are coated. Preferred, but non-limiting, examples of coated iron oxides are iron oxide, CI 77491; iron oxide, CI 77499 and iron oxide, CI 77492, each surface treated/coated with hydrogenated lecithin.

The following ingredients may be added to the above formulations to the indicated Phase in the indicated concentration range:

| Phase | Ingredient(s} | % wt/wt |
|---|---|---|
| A | *Capparis Spinosa* Fruit Extract, *Opuntia Ficus-indica* Extract, *Olea Europea* (Olive) Leaf Extract and Starch | 0.10-3.0 |
| A | *Olea Europea* (Olive) Fruit Extract and Starch | 0.10-3.0 |
| A | Carosine | 0.01-0.2 |
| C | Bisabolol and *Zingiber Officinale* (Ginger) Root Extract | 0.01-0.1 |
| C | Tocopheryl Acetate | 0.01-3.0 |
| E | PMMA, Cerium Oxide, Aluminum Oxide | 0.10-2.0 |
| E | Ubiquinone, Tocopheryl Acetate, $C_{12-15}$ Alkyl Benzoate | 0.25-2.0 |
| E | Water, Glycerin, Polygonum Aviculare Extract | 0.50-2.0 |
| E | Water, Glycerin, Camellia Oleifera Leaf Extract | 0.25-3.0 |

Combine Phase A ingredients. Heat and mix at 65-70° C. In a separate vessel, combine Phase B ingredients. Heat and mix at 40-50° C. Mix until ZnO is uniformly dispersed. Homogenize for approximately 8-10 minutes, until ZnO is coated with cetyl dimethicone and dimethicone.

Combine Phase C ingredients with Phase B ingredient. Mix until $TiO_2$ is uniform dispersed. Homogenize for approximately 1 minute. At 65-70° C., while mixing with high speed, very slowly add Phase A to the oil phase. Mix for 5-10 minutes. Homogenize for 1 minute. Add Phase D ingredient after homogenization; mix until uniformly dispersed. Continue mixing and cool mixture of A+B+C+D. When cooled to 50° C., add Phase E ingredients; mix until homogeneous. Cool final mixture A+B+C+D+E to 30° C.

The synergistic combination of ZnO and $TiO_2$ with (a) two SPF boosters—butyl octyl salicylate (BOS) and Sunspheres®, and (b) two siliceous compounds—an amorphous spherical silica and a mixture of diatomaceous algal species, each having photonic and porous silica crystals (Plankton Glass Flower®, "PGF"), in the ratios described above, achieve a critical wavelength ("CW") of at least 370 nm necessary to qualify as a "broad-spectrum" (UVA/UVB) sunscreen under applicable FDA regulations (as of the filing date of the present application). Combining these ingredients in ratios other than as described above do not achieve a critical wavelength of at least 370 nm.

| Prototype | CW (nm) | BOS | Sunspheres ® | ZnO | TiO2 | Silica | PGF |
|---|---|---|---|---|---|---|---|
| 1 | 368.13 | 13.00% | 2.50% | 10.00% | 3.50% | 2.50% | 0.50% |
| 2 | 371.80 | 13.00% | 5.50% | 10.00% | 3.50% | 2.00% | 0.50% |
| 3 | 375.88 | 13.00% | 5.50% | 10.00% | 3.50% | 2.50% | 0.50% |

While the illustrative embodiments of the invention have been described with particularity, it will be understood that various other modifications will be apparent to, and can be readily made by those skilled in the art, without departing from the spirit and scope of the invention. Accordingly, it is not intended that the scope of the claims appended hereto be limited to the examples and descriptions set forth hereinabove but rather that the claims be construed as encompassing all the features of patentable novelty in the present invention, including all features which would be treated as equivalents by persons having ordinary skill in the art of formulating topically-applied personal care and dermatological products.

The invention claimed is:

1. A broad-spectrum mineral sunscreen composition comprising a water-in-oil emulsion-based stable dispersion that comprises:

(1) a formulation component comprising (a) a water-in-oil emulsifier component (I) consisting of at least one polyglyceryl fatty acid ester compound containing 3-6 glycerin units, wherein the at least one polyglyceryl fatty acid ester compound is present in an amount of about 2 wt. % to about 6 wt. %, (II) wherein the water-in-oil emulsifier component is the only component in the composition that acts as an emulsifier, and (III) is free of any polyethylene glycol compounds, (b) a film-forming component consisting of a combination of two polysiloxane polymer compounds selected from (I) bis-vinyl dimethicone/dimethicone copolymer and (II) dimethicone and acrylates/dimethicone copolymer, wherein the combination of two polysiloxane polymer compounds is in an amount such that the film-forming component causes the composition to produce a continuous film on skin when applied thereto and wherein the film-forming component is the only component of the composition that is responsible for the formation of the film, and (c) a suspending dispersant component consisting of a mixture of disteardimonium hectorite, phenyl trimethicone, and triethyl citrate, wherein the suspending dispersant component makes up 1.5 wt. % to 3 wt. % of the composition, and (d) additional ingredients comprising polyhydroxystearic acid, dimethicone, and cetyl dimethicone, (2) a siliceous compound component consisting of (a) an amorphous spherical silica compound, and (b) a mixture of diatomaceous algae materials comprising materials from at least two of *Fragilaria zeilleri, Gomphonema angustatum, Navicula radiosa*, and *Cyclotella andancensis,* wherein the amorphous spherical silica compound and the mixture of diatomaceous algae materials are the only siliceous compound-containing materials in the composition, and (3) a sunscreen active ingredient component consisting of photoprotective metal oxide particles that block, reflect, refract, or otherwise attenuate ultraviolet radiation, the photoprotective metal oxide particles comprising (a) porous zinc oxide particles, wherein the porous zinc oxide particles (I) have an average particle size of greater than 100 nanometers and have an average particle size of less than about 800 nanometers, (II) comprise about 10 wt. % of the composition, and (III) are infiltrated by the formulation component in the composition, thereby significantly increasing the transparency of the porous zinc oxide particles in the composition, and (b) titanium dioxide particles, wherein (I) the zinc oxide particles and the titanium dioxide particles are evenly dispersed in the composition, (II) the composition does not separate into oil and water phases or experience particle agglomeration or particle settling after storage at an elevated temperature of 50° C. for one month or 40° C. for three months, (III) the composition provides a sun protection factor ("SPF") of at least 50, (IV) the composition is free of any small-molecule organic sunscreen active ingredients, (V) the composition does not cause visible whitening when applied to the skin of a person having a Fitzpatrick Skin Type of I-IV, and (VI) the composition has a critical wavelength of at least 370 nanometers.

2. The composition of claim 1, wherein the photoprotective metal oxide particles further comprise (a) aluminum oxide particles, (b) cerium oxide particles, or (c) both aluminum oxide particles and cerium oxide particles.

3. The composition of claim 2, wherein the photoprotective metal oxide particles further comprise iron oxide particles in an amount sufficient to impart a tint to the composition.

4. The composition of claim 1, wherein the titanium dioxide particles comprise about 3.5 wt. % of the composition.

5. The composition of claim 1, wherein the composition does not comprise (a) butyl octyl salicylate, (b) a styrene/acrylates copolymer, (c) polymethyl methacrylate, or (d) any combination of (a)-(c).

6. The composition of claim 1, wherein the composition further comprises squalane, and the squalane makes up about 0.5 wt. % to about 2 wt. % of the composition.

7. A method of applying the composition of claim 1 to the skin of a human to protect the skin of the human from solar radiation, wherein performing the method results in a reduction of dyschromia on the skin of the human.

8. The method of claim 7, wherein the method further provides (a) a reduction in appearance of fine lines or wrinkles on the skin of the human, (b) a reduction in the rate of trans-epidermal water loss on the skin of the human, (c) an increase of skin softness in the skin of the human, or (d) any combination of (a)-(c).

9. The composition of claim 2, wherein the photoprotective metal oxide particles comprise both aluminum oxide particles and cerium oxide particles which are included in the composition by the inclusion of an ingredient comprising a mixture of cerium oxide particles, aluminum oxide particles, and polymethyl methacrylate wherein the amount of the ingredient is equivalent to 0.1-2 wt. % of the composition.

10. The composition of claim 4, wherein the photoprotective metal oxide particles comprise both aluminum oxide particles and cerium oxide particles which are included in the composition by the inclusion of an ingredient comprising a mixture of cerium oxide particles, aluminum oxide particles, and polymethyl methacrylate wherein the amount of the ingredient is equivalent to 0.1-2 wt. % of the composition.

11. The composition of claim 6, wherein the photoprotective metal oxide particles comprise both aluminum oxide particles and cerium oxide particles which are included in the composition by the inclusion of an ingredient comprising a mixture of cerium oxide particles, aluminum oxide particles, and polymethyl methacrylate wherein the amount of the ingredient is equivalent to 0.1-2 wt. % of the composition.

12. The composition of claim 4, wherein the composition has a critical wavelength of about 375 nanometers or more.

13. The composition of claim 9, wherein the composition has a critical wavelength of about 375 nanometers or more.

14. The composition of claim 11, wherein the composition has a critical wavelength of about 375 nanometers or more.

15. The composition of claim 1, wherein the composition is water resistant for 80 minutes according to the test method of Section 352.76(b) of Title 21 of the United States Code of Federal Regulations in effect on Mar. 23, 2018.

16. The composition of claim 4, wherein the composition is water resistant for 80 minutes according to the test method of Section 352.76(b) of Title 21 of the United States Code of Federal Regulations in effect on Mar. 23, 2018.

17. The composition of claim 14, wherein the composition is water resistant for 80 minutes according to the test method of Section 352.76(b) of Title 21 of the United States Code of Federal Regulations in effect on Mar. 23, 2018.

* * * * *